United States Patent
Safai et al.

(10) Patent No.: US 7,307,431 B2
(45) Date of Patent: Dec. 11, 2007

(54) SYSTEM AND METHOD FOR MICROWAVE NON-DESTRUCTIVE INSPECTION

(75) Inventors: Morteza Safai, Seattle, WA (US); Gary E. Georgeson, Federal Way, WA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 11/213,568

(22) Filed: Aug. 26, 2005

(65) Prior Publication Data
US 2007/0046298 A1    Mar. 1, 2007

(51) Int. Cl.
*G01R 27/04* (2006.01)
*G01R 27/32* (2006.01)

(52) U.S. Cl. .................. 324/639; 324/638
(58) Field of Classification Search ............. 324/639, 324/638
See application file for complete search history.

(56) References Cited

U.S. PATENT DOCUMENTS

| | | | | |
|---|---|---|---|---|
| 4,634,963 | A * | 1/1987 | Lunden | 324/632 |
| 4,805,627 | A * | 2/1989 | Klingenbeck et al. | 600/425 |
| 5,798,521 | A * | 8/1998 | Froggatt | 250/227.19 |
| 6,005,916 | A * | 12/1999 | Johnson et al. | 378/87 |
| 6,026,173 | A | 2/2000 | Svenson | |
| 7,057,743 | B2 * | 6/2006 | Merkel et al. | 356/601 |
| 2003/0024315 | A1 | 2/2003 | Merkel et al. | |
| 2003/0034933 | A1 * | 2/2003 | Frenkel | 343/872 |

FOREIGN PATENT DOCUMENTS

WO    WO 02/18920 A1    3/2002

OTHER PUBLICATIONS

*TDR Composite Cure Monitoring*; © 2005 material Sensing & Instrumentation, Inc.; 5 pages; available at http://www.msi-sensing.com/tdr_composite.html (visited Aug. 16, 2005).
C P Neo et al., *Design and development of electromagnetic absorbers with carbon fiber composites and matching dielectric layers*; Smart Mater. Struct. 10 (2001), pp. 1107-1110, IOP Publishing Ltd, United Kingdom.

(Continued)

*Primary Examiner*—Anjan Deb
*Assistant Examiner*—Jeff Natalini
(74) *Attorney, Agent, or Firm*—Alston & Bird LLP (57) ABSTRACT

A system and method for inspecting a composite structure, such as to assess thermal degradation or resin curing, are provided in which the dielectric constant of the composite structure is determined using a microwave inverse scattering technique. The dielectric constant of the composite structure may be compared to the dielectric constant of one or more sample structures to determine the presence of thermal degradation or improper curing in the structure. In this regard, a system for inspecting a composite structure comprises a transmitter, a receiver, and a controller. The transmitter may be capable transmitting microwave energy directed toward the structure. The receiver may be capable of receiving microwave energy scattered from the structure. The controller may be capable of determining a dielectric constant of the structure using an inverse scattering algorithm and comparing the dielectric constant of the structure to a dielectric constant of at least one sample structure.

14 Claims, 3 Drawing Sheets

OTHER PUBLICATIONS

Cui et al., *Inverse Scattering of Two-Dimensional Dielectric Objects Buried in a lossy Earth using the Distorted Born Iterative Method*, Transactions On Geoscience And Remote Sensing, vol. 39, No. 2, Feb. 2001, pp. 339-345.

Van Den Berg et al., *Image Reconstruction from Ipswich Data—III*, IEEE Antennas and Propagation Magazine, vol. 41, N. 2, Apr. 1999, pp. 27-32.

Merkel, *Inverse Scattering Algorithm For Microwave Tomography Applications*, October Biometrics AG, 10 pages.

Weedon et al., *Broadband Microwave Inverse Scattering For Nondestructive Evaluation (NDE)*, Review of Progress in Quantitative Nondestructive Evaluation, vol. 13 (1994), pp. 615-622.

Jietao Zhang, Mansor Nakhkash, Yi Huang, *Electromagnetic imaging of layered building materials*, Measurement Science And Technology, IOP, Bristol, GB; vol. 12, No. 8, Aug. 1, 2001, pp. 1147-1152.

Nasser Qaddoumi, Gary Carriveau, Stoyan Ganchev, Reza Zoughi, *Microwave Imaging of Thick Composite Panels With Defects*, Materials Evaluation, vol. 53, No. 8, May 1994, pp. 926-929.

Stoyan I. Ganchev, *Nondestructive Microwave Measurement of Dielectric Materials*, 12th International Conference On Microwaves And Radar, Mikon-98, Conference Proceedings, vol. 3, 1998, pp. 687-691.

PCT/US2006/032915, International Search Report, mailed Feb. 1, 2007.

\* cited by examiner

SYSTEM AND METHOD FOR MICROWAVE NON-DESTRUCTIVE INSPECTION

FIELD OF THE INVENTION

The present invention relates generally to systems and methods for inspecting a composite structure and, more particularly, to a system and method for non-destructive microwave inspection of a composite structure.

BACKGROUND OF THE INVENTION

Non-destructive inspection (NDI) of structures involves thoroughly examining a structure without harming the structure or requiring its significant disassembly. Non-destructive inspection is typically preferred to avoid the schedule, labor, and costs associated with removal of a part for inspection, as well as avoidance of the potential for damaging the structure. Non-destructive inspection is advantageous for many applications in which a thorough inspection of the exterior and/or interior of a structure is required. For example, non-destructive inspection is commonly used in the aircraft industry to inspect aircraft structures for any type of internal or external damage to or defects (flaws) in the structure. Inspection may be performed during manufacturing or after the completed structure has been put into service, including field testing, to validate the integrity and fitness of the structure. In the field, access to interior surfaces of the structure is often restricted, requiring disassembly of the structure, introducing additional time and labor.

Among the structures that are routinely non-destructively tested are composite structures, such as composite sandwich structures and other adhesive bonded panels and assemblies and structures with contoured surfaces. These composite structures, and a shift toward lightweight composite and bonded materials such as using graphite materials, create a need for devices and processes to ensure structural integrity, production quality, and life-cycle support for safe and reliable use. As such, it is frequently desirable to inspect structures to identify any defects, such as cracks, discontinuities, voids, or porosity, which could adversely affect the performance of the structure. For example, a defect in composite sandwich structure comprising one or more layers of lightweight honeycomb or foam core material with composite or metal skins bonded to each side of the core, may include disbonds which may occur at the interfaces between the core and the skin or between the core and a buried septum.

Advanced composite materials, such as carbon fiber composites, are increasingly used in the manufacture of aircraft. Carbon fiber composite panels may be used to create, for example, the fuselage, the nose, and/or the wing structures of aircraft. Carbon fiber composite panels are typically created by combining layers of carbon fiber with a resin, such as a polyester epoxy resin, that binds the fibers together. The resin is typically heat cured, at temperatures and for lengths of time that are precisely predefined. All materials have acceptable operating ranges or envelopes for their properties. Composite materials in general and more particularly composite materials used for aircraft surfaces and structures have defined operating envelopes for their properties. Materials satisfying the envelope criteria are acceptable for use. Materials that exceed the envelope criteria may need to be refurbished, repaired or replaced. Material properties can be altered by any of a number of factors. Heat based influences include fire, lightning, or exhaust impingement. Mechanical influences can include actual impact as well as other stresses to the composite structure such as pressure. Environmental degradation due to sunlight, rain, or salt spray may also occur.

When composite sections are repaired in place (i.e., without removing the damaged or degraded section from the aircraft) and when a particular part warrants additional inspection, it may be desirable to inspect the repaired material to ensure that the properties of the resulting material are within the operating envelope. Inspection may help insure that the repaired composite material as well as the original manufacture of the composite material and their constituent resins were cured in accordance with specifications. In addition to carbon fiber composites, other composite materials, such as fiberglass and ceramic composites, may also benefit from inspection for material property changes due to for instance heat degradation or mechanical stress and/or improper curing during repair.

Current methods exist to detect discrete damage in composite materials. However, existing methods of non-destructively detecting heat degradation are only capable of detecting heat degradation to the surface of the composite structure. In order to measure heat degradation that may exist below the surface, the plies of the composite structure need to be removed sequentially in order to determine how deep the damage is.

BRIEF SUMMARY OF THE INVENTION

A system and method for inspecting a composite structure to assess material properties is provided in which the dielectric constant of the composite structure is determined using a microwave inverse scattering technique. The material properties can be established during manufacture such as initial resin curing of a composite structure or alternatively through heat degradation or mechanical stress applied to the structure during use. The system and method for inspecting a composite structure compares the dielectric constant of the composite structure to the dielectric constant of one or more sample structures to determine the material properties which in turn may indicate whether the structure has experienced thermal degrade and/or exhibits a manufacturing inconsistency.

In this regard, a system for inspecting a composite structure, to assess material properties of the composite structure, comprises a transmitter, a receiver, and a controller. The transmitter may be capable transmitting microwave energy directed toward the structure. The receiver may be capable of receiving microwave energy scattered from the structure. The controller may be capable of determining a dielectric constant of the structure using an inverse scattering algorithm and comparing the dielectric constant of the structure to a dielectric constant of at least one sample structure.

Sample structure may be selected from the group comprising a sample with known properties, a properly cured sample, a thermally degraded sample, and an improperly cured sample. In one embodiment, for example, the sample structure may be selected from the group comprising a sample with known properties, a properly cured sample, a first thermally degraded sample exhibiting a first set of properties, and a second thermally degraded sample exhibiting a second set of properties.

In one embodiment, the transmitter is further capable of transmitting microwave energy directed toward the sample structure. The receiver may be further capable of receiving microwave energy scattered from the sample structure. The controller may be further capable of evaluating the received energy and determining the dielectric constant of the sample structure using an inverse scattering algorithm.

The transmitter may be further capable of transmitting microwave energy having a plurality of wavelengths directed toward the structure. The receiver may be further capable of receiving microwave energy having a plurality of wavelengths scattered from the structure. The controller may be further capable of determining a dielectric constant of the structure at each of the plurality of wavelengths and determining which of the plurality of wavelengths corresponds to a maximum dielectric constant. The transmitter may then transmit microwave energy having a wavelength corresponding to the maximum dielectric constant, and the receiver may receive microwave energy scattered from the structure having a wavelength corresponding to the maximum dielectric constant.

In addition to the system for inspecting a composite structure as described above, other aspects of the invention are directed to corresponding methods for inspecting a composite structure.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

Embodiments of the invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Embodiments of the invention are capable of inspecting a composite structure, to assess material properties that are influenced by thermal degradation or resin curing of the composite structure, by determining the dielectric constant of the composite structure. A composite structure will typically have a dielectric constant that is approximately equal to the dielectric constant of any other composite structure that has been similarly constructed. However, a composite structure that has been thermally degraded will typically have a measurably different dielectric constant than a similarly constructed but non-thermally degraded structure at the same temperature and humidity. Similarly, a composite structure in which the resin has been improperly cured during repair will typically have a measurably different dielectric constant than a similarly constructed but properly cured structure at the same temperature and humidity. Thermal degradation and excessive curing typically change the dielectric constant of a composite structure. Additionally, insufficient curing of an in-place repair will typically result in a measurably different dielectric constant as compared to a properly cured repair at the same temperature and humidity.

Thermal degradation may encompass both damage of the structure to the point of microcracking or delamination as well as degradation of the composite matrix due to excessive heat, resulting in a reduction of material property values that are important to the structure's mechanical performance.

The dielectric constant may be measured using a microwave inverse scattering technique, such as those described in *Inverse Scattering of Two-Dimensional Dielectric Objects Buried in a Lossy Earth Using the Distorted Born Iterative Method*, Tie Jun Cui et al., Transactions on Geoscience and Remote Sensing, Vol. 39, No. 2 (February 2001); *Image Reconstruction from Ipswich Data—III*, P. M. van den Berg et al., IEEE Antennas and Propagation Magazine, Vol. 41, No. 2 (April 1999); *Inverse Scattering Algorithm for Microwave Tomography Applications*, Harald F. Merkel, Biometrics AB; and U.S. Patent Application Publication No. 2003/0024315, entitled Device, Method and System for Measuring the Distribution of Selected Properties in a Material, filed Dec. 4, 2000 and published Feb. 6, 2003, the contents of which are incorporated herein in their entirety.

Embodiments of the invention may be used to inspect structures made of many different types of composite materials, such as carbon fiber, fiberglass, and ceramic. Additionally, materials used to coat surfaces, such as radar absorbing materials and thermal protection materials, may also be inspected using embodiments of the invention. Any structure or material that is at least partially absorptive of microwave energy may be inspected using embodiments of the invention.

The dielectric constant of a structure that has potentially been thermally degraded may be compared to the dielectric constant of a sample structure that is known to be non-degraded and/or to the dielectric constant of a sample structure that is known to be thermally degraded. If the dielectric constant of the potentially degraded structure is approximately equal to the dielectric constant of the known non-degraded sample, then this indicates that the potentially degraded structure is likely not degraded. However, if the dielectric constant of the potentially degraded structure is approximately equal to the dielectric constant of the known degraded sample, then this indicates that the potentially degraded structure is likely degraded.

Similarly, the dielectric constant of a structure that has potentially been improperly cured (either over-cured or under-cured) during repair may be compared to the dielectric constant of a sample structure that is known to be properly cured during repair and to the dielectric constant of a sample structure that is known to be improperly cured during repair. If the dielectric constant of the potentially improperly cured structure is approximately equal to the dielectric constant of the known properly cured sample, then this indicates that the potentially improperly cured structure is likely properly cured. However, if the dielectric constant of the potentially improperly cured structure is approximately equal to the dielectric constant of the known improperly cured sample (either over-cured or under-cured), then this indicates that the potentially improperly cured structure is likely to have been improperly cured during repair. It is typically preferable to compare the dielectric constant of a structure that has potentially been improperly cured during repair to the dielectric constant of a sample structure that is known to be properly cured during repair. However, if such a repaired and properly cured sample is not available, a similar result may be obtained by comparing the dielectric constant of the structure that has potentially been improperly cured during repair to the dielectric constant of a sample structure that has not been repaired at all).

Hereinafter, structures to be tested that have potentially either been thermally degraded or improperly cured during repair will be collectively referred to as "test structures," sample structures that are either known to have material properties that are indicative of parts that are either non-degraded or known to be properly cured during repair will be collectively referred to as "known desirable samples," and sample structures that have material properties that are indicative of parts that are either known to be degraded or known to be improperly cured during repair will be collectively referred to as "known undesirable samples."

The dielectric constant of a test structure may be compared to the dielectric constants of one known desirable sample and one known undesirable sample, as described above. Alternatively, the dielectric constant of a test structure may be compared to the dielectric constants of one known desirable sample and two or more known undesirable samples. For example, one known undesirable sample may have moderate thermal degradation and another known undesirable sample may have significant thermal degradation. By comparing the dielectric constant of the test structure to the dielectric constants of two or more known undesirable samples with different amounts of degradation, the amount of degradation to the test structure (if any) may be estimated.

The sample structures would typically correspond closely to the structure that is to be inspected in terms of materials and fabrication process. For example, if the fuselage of one type of aircraft is to be inspected, the sample structure would typically be created from the same materials and using the same process as was used to create the fuselage of that particular type of aircraft. Such a sample would typically not be used in the inspection of the wing of that type of aircraft or in the inspection of the fuselage of another type of aircraft. Differing materials and methods in the manufacture of different structures within one type of aircraft, or in similar structures within different types of aircraft, and the corresponding differences in the dielectric constants of the structures, typically necessitate such correspondence between the samples and the structure to be inspected. The amount of fiber, the type and amount of adhesive, the curing temperature of the adhesive, and presence of radar absorbing material or copper mesh within the composite material are examples of factors that may vary and thus may necessitate such correspondence. Depending on the complexity of a particular geometry of the structure that is to be inspected, it may be necessary to use a sample that the same geometric configuration as the structure that is to be inspected. This use of a sample with the same geometric configuration as the structure to be inspected may be required, for example, when inspecting corners or areas where different types of structures are joined.

The dielectric constants of the known desirable samples and the known undesirable samples may be determined in advance of the inspection of the test structure and stored in a database, and the dielectric constants may be retrieved from the database at a future time for comparison to the dielectric constant of a test structure. As such, an inspection may be performed without having physical possession of the samples. Alternatively, the dielectric constants of the known desirable samples and the known undesirable samples may be determined at approximately the same time as the inspection of the test structure. This alternative method typically requires physical possession of the samples at the time of the inspection. However, determining the dielectric constants of the samples and the test structure using the same equipment may ensure that faulty or differently calibrated equipment does not cause an incorrect determination of degradation or improper curing.

Figure 1:
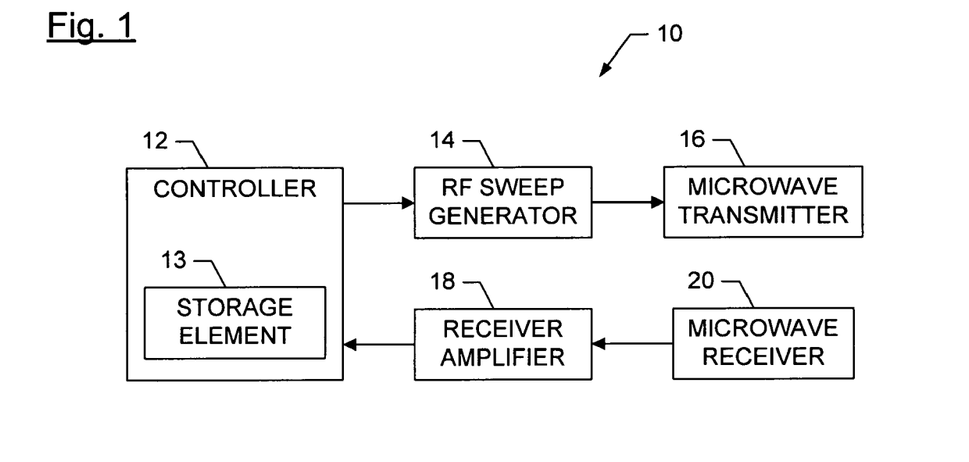
FIG. 1 is a functional block diagram of a system for inspecting a composite structure, according to one embodiment of the invention.

Referring now to FIG. 1, a functional block diagram of a system for inspecting a composite structure is illustrated, according to one embodiment of the invention. The system 10 comprises a controller 12, a radio frequency (RF) sweep generator 14, a microwave transmitter 16, a receiver amplifier 18, and a microwave receiver 20. The controller 12 could be, for example, a computing device, central processing unit, processor, programmable gate array, or any other device that is capable of controlling such a system. The controller 12 may include a storage element 13 for storing the dielectric constants of the samples as discussed above. The controller 12 will typically send a signal to the RF sweep generator 14 indicating the desired wavelength(s) of the RF signal to be transmitted at the structure to be inspected. As discussed in detail below, the RF signal may have a single wavelength or multiple wavelengths. The RF sweep generator 14 will typically create a signal having a waveform corresponding to the desired wavelength and used to drive the microwave transmitter 16. As a result of receiving the signal from the RF sweep generator, the microwave transmitter transmits RF energy having the desired wavelength in the microwave band. The microwave band generally corresponds to wavelengths approximately in the range of 30 centimeters (corresponding to a frequency of 1 gigahertz (GHz)) to 1 millimeter (corresponding to a frequency of 300 GHz). Typically the scanning frequencies will be from 8–14 GHz, depending on the structural characteristics of the inspected structure.

Some of the microwave energy that is transmitted by the transmitter 16 is scattered off the surface to be inspected and received by the microwave receiver 20. The received signal is typically sent to an amplifier 18 where it is amplified and then sent to the controller. By comparing the transmitted signal and the received signal, the controller is able to use a microwave inverse scattering technique to determine the dielectric constant of the surface that scattered the microwave energy.

Figure 2A:
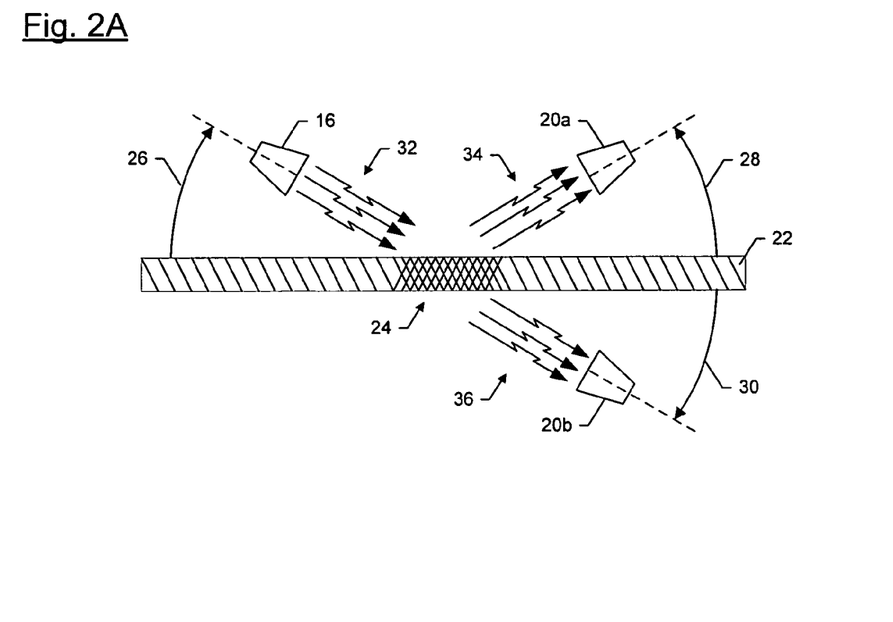
FIG. 2A is side sectional view of a composite structure being inspected by the system of FIG. 1.

Referring now to FIG. 2A, a sectional view of a composite structure being inspected by the system of FIG. 1 is illustrated. The composite structure 22 may be, for example, an aircraft wing or fuselage. The structure 22 may have an area 24 that is potentially degraded or that has been repaired in place. Embodiments of the invention may be used to determine if area 24 has been thermally degraded, or if a prior repair was improperly cured. Microwave transmitter 16 is typically placed at an angle 26 relative to the surface 22 to be inspected, and located in a position such that the microwave energy 32 transmitted from the transmitter is directed toward the area 24 to be inspected. The power output of the microwave transmitter may be approximately one milliwatt. The microwave receiver may be located on the same side of the structure 22 as the transmitter (as shown by receiver 20*a*), such that the receiver may receive microwave energy 34 that is scattered off the surface. The receiver 20*a* would typically be placed at an angle 28 relative to the surface, angle 28 being substantially equal to the angle 26 of the transmitter. The angle of the transmitter and the receiver relative to the surface may vary. In one exemplary embodiment, the angle may vary from 15 degrees to 90 degrees, and preferably be about 45 degrees. Alternatively, the receiver may be located on the opposite side of the structure from the transmitter (as shown by receiver 20*b*) such that the receiver may receive microwave energy 36 that passes through the surface. The receiver 20*b* would typically be placed at an angle 30 relative to the surface, angle 30 being substantially equal to the angle 26 of the transmitter. In an alternative embodiment of the invention, two or more receivers may be located together on one side of the structure, either on the same side of the structure as the transmitter or the opposite side.

Figure 2B:
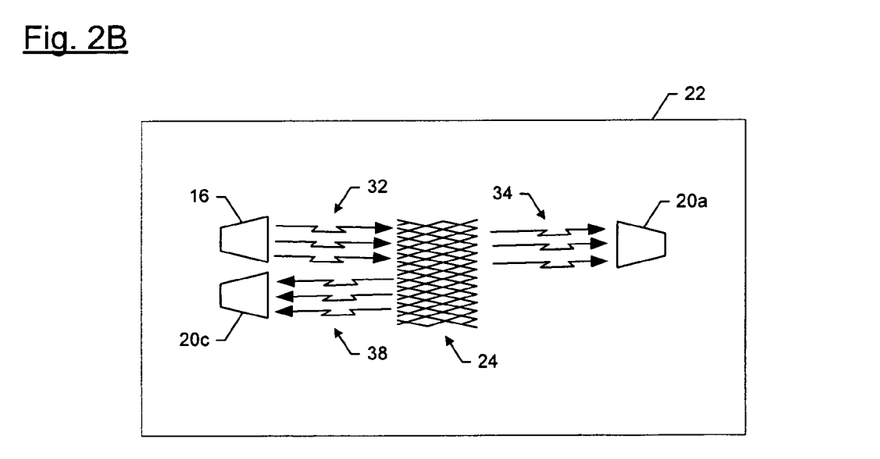
FIG. 2B is top view of a composite structure being inspected by the system of FIG. 1.

Referring now to FIG. 2B, a top view of a composite structure being inspected by the system of FIG. 1 is illustrated. Similar to FIG. 2A, FIG. 2B illustrates a microwave transmitter 16 transmitting microwave energy 32 toward the area 24 to be inspected. Microwave receiver 20*a* is located on the same side of the structure 22 as the transmitter but on the opposite side of the area 24 to be inspected, such that the receiver may receive microwave energy 34 that is scattered off the surface. Microwave receiver 20*c* is located on the same side of the structure 22 as the transmitter and on the same side of the area 24 to be inspected, such that the receiver may receive microwave energy 38 that is scattered off the surface. Microwave transmitter 16 and microwave receiver 20*c* may be positioned substantially parallel to each other, as illustrated in FIG. 2B, if the area 24 to be inspected is relatively large. The benefit of a parallel (or nearly parallel) configuration of the transmitter and receiver is that such a configuration enables both the transmitter and receiver to be mounted in a single inspection head. Alternatively, microwave transmitter 16 and microwave receiver 20*c* may be positioned at an acute angle relative to each other (not illustrated) and aimed toward the area to be inspected if the area to be inspected is relatively small.

Figure 3:
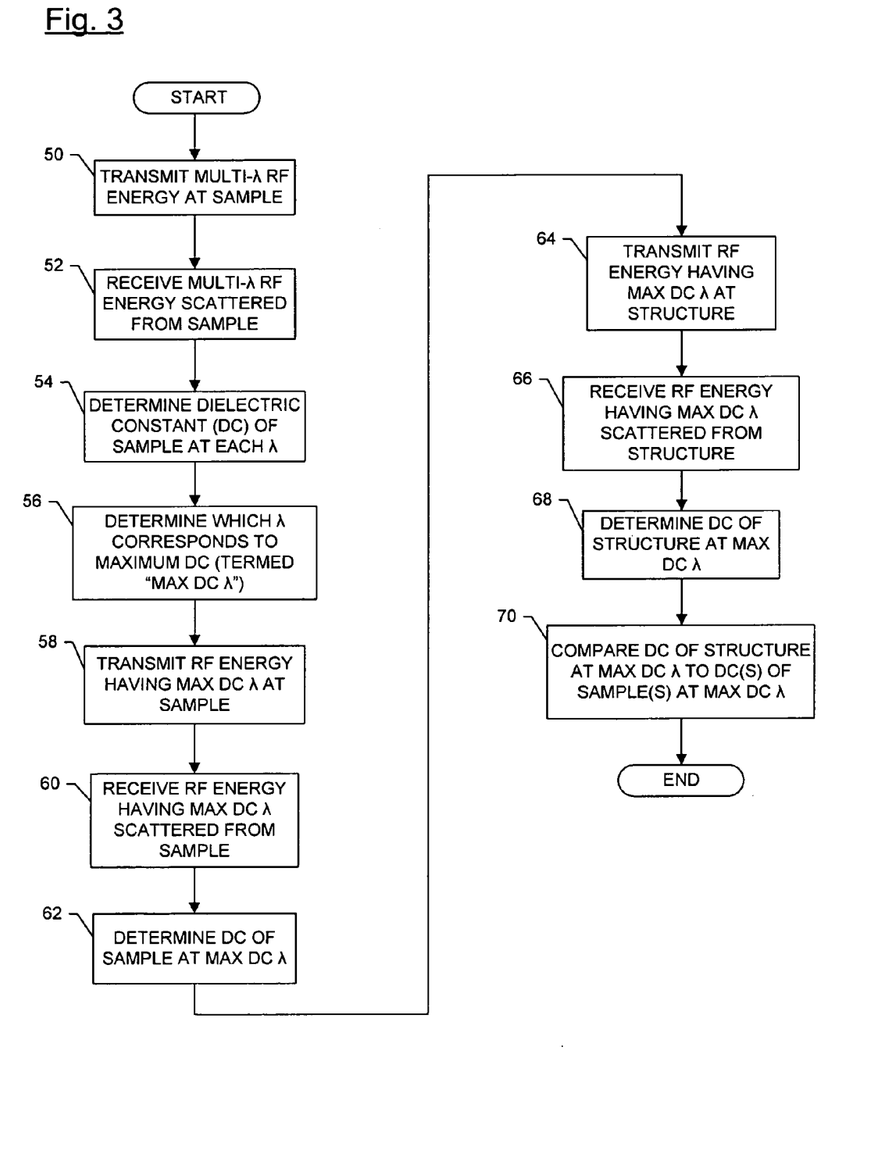
FIG. 3 is a flowchart of a method of inspecting a composite structure, according to one embodiment of the invention.

Referring now to FIG. 3, a flowchart of a method of inspecting a composite structure is illustrated, according to one embodiment of the invention. As discussed above, the dielectric constants of the samples (i.e., the known desirable sample and the known undesirable sample(s)) may be determined in advance and stored in a database or may be determined close to the time the dielectric constant of the test structure is determined. In the embodiment of the invention illustrated in FIG. 3, the dielectric constants of the samples are determined close to the time the dielectric constant of the test structure is determined. Several factors, such as the composition of the structure and any contamination on the surface of the samples and the structure, may affect which wavelength of microwave energy is optimum for determining the dielectric constant of the samples and the structure. Therefore, it may be desirable to transmit multiple wavelength microwave energy to determine the optimum wavelength. In one embodiment of the invention, the optimum wavelength for determining the dielectric constant may be determined in advance to enable single wavelength scanning (at the predetermined optimum wavelength) at the time of the inspection. In the alternative embodiment illustrated in FIG. 3, the optimum wavelength may be determined at the time of inspection. Multiple wavelength ("mult-$\lambda$") RF energy may be transmitted, such as by a microwave transmitter, at a sample. See block 50. In one exemplary embodiment, the transmitted multi-$\lambda$ energy may comprise 7 different wavelengths over a frequency range of 8 to 14 GHz, in increments of approximately 1 GHz (e.g., 8.0 GHz, 9.0 GHz, 10.0 GHz, and so on through 14 GHz). The multiple wavelength microwave energy scattered from the sample may be received, such as by a microwave receiver. See block 52. The dielectric constant of the sample may be determined at each wavelength, such as by the controller 12 of the system of FIG. 1. See block 54. The controller may then determine which wavelength corresponds to the maximum determined dielectric constant of the sample (this may be termed the "maximum dielectric constant wavelength" or "max DC $\lambda$"). See block 56. After the max DC $\lambda$ is determined, RF energy at the max DC $\lambda$ may be transmitted by a microwave transmitter at the sample. See block 58. The microwave energy at the max DC $\lambda$ that is scattered from the sample may be received, such as by a microwave receiver. See block 60. The dielectric constant of the sample at the max DC $\lambda$ may be determined by the controller. See block 62. Although not illustrated, blocks 50 through 62 would typically be repeated for each sample to obtain the dielectric constant of each sample. In an embodiment of the invention in which the optimum wavelength (i.e., the max DC $\lambda$) is predetermined, single wavelength microwave energy may be transmitted, received, and used to determine the dielectric constant of the sample, and blocks 50 through 56 may be omitted. In an embodiment of the invention in which the dielectric constants of the samples is predetermined, blocks 50 through 62 may be omitted. Determining the max DC $\lambda$ and the dielectric constant at the max DC $\lambda$ (and, as discussed below, determining the dielectric constant of the structure at the max DC $\lambda$) may increase the likelihood of accurately determining the dielectric constant and therefore accurately comparing the sample to the test structure and determining degradation or improper curing.

After the max DC $\lambda$ is determined and the dielectric constants of the samples at the max DC $\lambda$ are determined, microwave energy at the max DC $\lambda$ may be transmitted by a microwave transmitter at the test structure. See block 64. The microwave energy scattered from the test structure may be received, such as by a microwave receiver. See block 66. The dielectric constant of the test structure at the max DC $\lambda$ may be determined by the controller. See block 68. The dielectric constant of the test structure may be compared to the dielectric constants of the samples. See block 70. As discussed above, comparing the dielectric constant of the test structure to the dielectric constants of the samples may indicate whether the test structure is in fact degraded or has been properly cured depending on which sample's dielectric constant is nearly equal to the dielectric constant of the test structure.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system for inspecting a composite structure comprised of a material, the system comprising:
   a transmitter capable of transmitting microwave energy directed toward the structure;
   a receiver capable of receiving microwave energy scattered from the structure; and
   a controller connected to the receiver for analyzing the microwave energy scattered from the structure, the controller capable of determining a dielectric constant of the structure using an inverse scattering algorithm and comparing the dielectric constant of the structure to a dielectric constant of at least one sample structure that is comprised of the same material as the composite structure, wherein the composite structure and the at least one sample structure are separate structures such that the transmitter is configured to transmit microwave energy toward the composite structure without also concurrently irradiating the at least one sample structure.

2. The system of claim 1, wherein the at least one sample structure is selected from the group comprising a non-degraded sample, a properly cured sample, a thermally degraded sample, and an improperly cured sample.

3. The system of claim 1, wherein the at least one sample structure is selected from the group comprising a non-degraded sample, a properly cured sample, a first thermally degraded sample, a second thermally degraded sample having a differing amount of degradation than the first thermally degraded sample, a first improperly cured sample, and a second improperly cured sample having a differing amount of improper curing than the first improperly cured sample.

4. The system of claim 1, wherein the transmitter is further capable of transmitting microwave energy directed toward the at least one sample structure; wherein the receiver is further capable of receiving microwave energy scattered from the at least one sample structure; and wherein the controller is further capable of determining the dielectric constant of the at least one sample structure using an inverse scattering algorithm.

5. A system for inspecting a composite structure, the system comprising:
 a transmitter capable of transmitting microwave energy having a plurality of wavelengths directed toward the structure; and
 a receiver capable of receiving microwave energy having a plurality of wavelengths scattered from the structure; and
 a controller connected to the receiver for analyzing the microwave energy scattered from the structure, the controller capable of determining a dielectric constant of the structure at each of the plurality of wavelengths and determining which of the plurality of wavelengths corresponds to a maximum dielectric constant; wherein the transmitter is thereafter capable of transmitting microwave energy directed toward the structure by transmitting microwave energy having a wavelength corresponding to the maximum dielectric constant; and wherein the receiver is thereafter capable of receiving microwave energy scattered from the structure by receiving microwave energy having a wavelength corresponding to the maximum dielectric constant.

6. A method for inspecting a composite structure comprised of a material, the method comprising:
 transmitting microwave energy directed toward the structure;
 receiving microwave energy scattered from the structure;
 determining a dielectric constant of the structure using an inverse scattering algorithm; and
 comparing the dielectric constant of the structure to a dielectric constant of at least one sample structure that is comprised of the same material as the composite structure,
 wherein the composite structure and the at least one sample structure are separate structures such that transmitting microwave energy comprises transmitting microwave energy toward the composite structure without also concurrently irradiating the at least one sample structure.

7. The method of claim 6, wherein the at least one sample structure is selected from the group comprising a non-degraded sample, a properly cured sample, a thermally degraded sample, and an improperly cured sample.

8. The method of claim 6, wherein the at least one sample structure is selected from the group comprising a non-degraded sample, a properly cured sample, a first thermally degraded sample, a second thermally degraded sample having a differing amount of degradation than the first thermally degraded sample, a first improperly cured sample, and a second improperly cured sample having a differing amount of improper curing than the first improperly cured sample.

9. The method of claim 6, further comprising:
 transmitting microwave energy directed toward the at least one sample structure;
 receiving microwave energy scattered from the at least one sample structure; and
 determining the dielectric constant of the at least one sample structure using an inverse scattering algorithm.

10. A method for inspecting a composite structure, the method comprising:
 transmitting microwave energy having a plurality of wavelengths directed toward the structure;
 receiving microwave energy having a plurality of wavelengths scattered from the structure;
 determining a dielectric constant of the structure at each of the plurality of wavelengths; and
 determining which of the plurality of wavelengths corresponds to a maximum dielectric constant;
 transmitting microwave energy directed toward the structure at a wavelength corresponding to the maximum dielectric constant;
 receiving microwave energy scattered from the structure and having a wavelength corresponding to the maximum dielectric constant;
 determining a dielectric constant of the structure at the wavelength corresponding to the maximum dielectric constant; and
 comparing the dielectric constant of the structure at the wavelength corresponding to the maximum dielectric constant to a dielectric constant of at least one sample structure.

11. A system for inspecting a composite structure, the system comprising:
 a transmitter capable of transmitting microwave energy having a plurality of wavelengths directed toward the structure;
 a receiver capable of receiving microwave energy having a plurality of wavelengths scattered from the structure; and
 a controller capable of determining a dielectric constant of the structure at each of the plurality of wavelengths and determining which of the plurality of wavelengths corresponds to a maximum dielectric constant;
 wherein the transmitter is thereafter capable of transmitting microwave energy having a wavelength corresponding to the maximum dielectric constant directed toward the structure; wherein the receiver is thereafter capable of receiving microwave energy having a wavelength corresponding to the maximum dielectric constant; and wherein the controller is thereafter capable of determining a dielectric constant of the structure at the wavelength corresponding to the maximum dielectric constant and comparing the dielectric constant of the structure at the wavelength corresponding to the maximum dielectric constant to a dielectric constant of at least one sample structure.

12. The system of claim 11, wherein the at least one sample structure is selected from the group comprising a non-degraded sample, a properly cured sample, a thermally degraded sample, and an improperly cured sample.

13. The system of claim 11, wherein the at least one sample structure is selected from the group comprising a non-degraded sample, a properly cured sample, a first thermally degraded sample, a second thermally degraded sample having a differing amount of degradation than the first thermally degraded sample, a first improperly cured sample, and a second improperly cured sample having a differing amount of improper curing than the first improperly cured sample.

14. The system of claim 11, wherein the transmitter is further capable of transmitting microwave energy directed toward the at least one sample structure; wherein the receiver is further capable of receiving microwave energy scattered from the at least one sample structure; and wherein the controller is further capable of determining the dielectric constant of the at least one sample structure using an inverse scattering algorithm.

* * * * *